United States Patent [19]

Fedter et al.

[11] Patent Number: 4,752,855
[45] Date of Patent: Jun. 21, 1988

[54] CAPACITATIVE-TYPE HUMIDITY SENSING ELEMENT AND SYSTEM, AND METHOD OF MANUFACTURE

[75] Inventors: Horst Fedter, Bühlertal; Werner Grunwald, Gerlingen; Peter Nolting, Bühlertal; Claudio De La Prieta, Stuttgart; Kurt Schmid, Ditzingen-Schöckingen, all of Fed. Rep. of Germany

[73] Assignee: Robert Bosch GmbH, Stuttgart, Fed. Rep. of Germany

[21] Appl. No.: 26,866

[22] Filed: Mar. 17, 1987

[30] Foreign Application Priority Data

Apr. 16, 1986 [DE] Fed. Rep. of Germany ....... 3612727

[51] Int. Cl.$^4$ .............................................. H01G 5/00
[52] U.S. Cl. .................................................. 361/286
[58] Field of Search ...................... 73/335, 336, 336.5, 73/29; 252/518, 521; 338/35; 236/44 A; 29/25.41; 361/286

[56] References Cited

U.S. PATENT DOCUMENTS

| 4,041,437 | 8/1977 | Matsuura et al. | 73/336.5 |
| 4,046,074 | 9/1977 | Hochberg et al. | 346/135.1 |
| 4,196,338 | 4/1980 | Edel | 73/73 |
| 4,424,933 | 1/1984 | Sutoh et al. | 236/44 A |
| 4,464,647 | 8/1984 | Yokomizo et al. | 73/336 |
| 4,656,455 | 4/1987 | Tanino et al. | 73/29 |

FOREIGN PATENT DOCUMENTS 0210601  12/1982  Japan ..................................... 338/35

OTHER PUBLICATIONS

Leppavuori, "New Thick Film Sensors", Electrocomponent Science and Technology, vol. 6, pp. 193–197, 1980.

Jones et al., "A Barium Fluoride Film Hygrometer Element", Journal of Geophysical Research, vol. 65, No. 7, Jul. 1960.

"Thick Film Circuits: Present State and Future Development", J. Novotny, Electrocomponent Science and Technology, 1981, vol. 9, pp. 131–137.

Primary Examiner—Stewart J. Levy
Assistant Examiner—Robert R. Raevis
Attorney, Agent, or Firm—Frishauf, Holtz, Goodman & Woodward

[57] ABSTRACT

A humidity sensor, and particularly a sensor which can distinguish between low humidity values, for example below 60% humidity, and high humidity values, for example 90% humidity and thereover, and change the capacitance between output electrodes (5, 6) is formed by applying interdigited comb electrodes (1, 2) on a substrate (8) and applying over the substrate a ceramic mass formed of $BaRuO_3$, $V_2O_5$ and $Na_2WO_4$, with a weight relationship of $(1\pm0.4):(1\pm0.4):(0.6\pm0.2)$ preferably 1:1:0.6. The sensor is made by first making a powder of the components, mixing it with a glass paste and, if necessary, a thinner, and applying the resulting paste by thick-film technology to a ceramic substrate on which the electrodes have been applied, and then firing the substrate at a temperature of between 550° C. to 850° C. The sensor is particularly sensitive in humidity ranges above 60% relative humidity and is especially suitable to sense fogging of the inside of a windshield of an automotive vehicle.

16 Claims, 2 Drawing Sheets

CAPACITATIVE-TYPE HUMIDITY SENSING ELEMENT AND SYSTEM, AND METHOD OF MANUFACTURE

The present invention relates to a sensor and a system to sense relative humidity, and more particularly to a humidity sensor and a system in which it is being used, by providing an element, the capacitance of which changes upon change in relative humidity, which capacitance change can then be evaluated to provide a relative humidity output signal.

BACKGROUND

Various types of humidity sensors operating on the capacitative principle are known. Usually, a plastic foil is provided which, reversibly, is capable of accepting and giving off water vapor. Upon change in the water vapor retained by the foil, the capacitance of the sensor with which it is connected will change. The change in capacitance is evaluated by a capacitative sensing circuit, for example a capacitative measuring bridge.

Sensors of this type are mechanically sensitive since polymer foils are used therein. The electrodes used with such a sensor are, at least in part, vapor deposited on the polymer foil. Manufacture of such sensing elements, hence, is expensive. Sensors of this type are thus not suitable structures for mass production or mass use. It has been found that in ranges of high relative humidity, that is, humidity of 90% or more, erroneous measurements can be obtained due to secondary sorption effects, which remain within the foil and are not readily dissipated even if ambient humidity should drop.

THE INVENTION

It is an object to provide a humidity sensor, and especially a humidity sensor which is sturdy and reliable, and mechanically strong, so that it can be used in ambient environments subject to shock and vibration, for example within an automotive vehicle; and to provide a method for its manufacture.

Briefly, a mixture of $BaRuO_3$, $V_2O_5$ and $Na_2WO_4$ is homogenized, presintered, added to a glass paste to form an application paste, for example suitable for thick-film printing technology. The so-made application paste is then applied on a ceramic substrate, for example $Al_2O_3$, on which electrodes, preferably in form of interdigited double-comb construction have been applied, and sintered on the substrate.

The resulting structure will be a humidity sensor with substantial advantages over previously used polymer-foil humidity sensors. Manufacture of the sensor structure is simple so that it can be made in large quantities by inexpensive production processes. Since the substrate for the sensor will be a ceramic, it is essentially immune to mechanical damage and, particularly in the region of relatively high humidity, will provide good results.

In accordance with a preferred feature of the invention, the proportion of $BaRuO_3$, $V_2O_5$ and $Na_2WO_4$ is present in 1:1:0.6, for example with tolerances of $(1\pm0.4):(1\pm0.4):(0.6\pm0.2)$; lesser tolerances are preferred.

In the above relationship, and in the discussion and claims that follow, all relative relationships are by weight.

In accordance with a preferred feature of the invention, the homogenized mixture is ground to a fine powder and a glass paste is added as a binder, together with a thinner or solvent to form a printable paste, to permit application of the paste material on the substrate with the electrodes thereon by well known thick-film technology.

DRAWINGS

DETAILED DESCRIPTION

The three basic components, $BaRuO_3$, $V_2O_5$ and $Na_2WO_4$ are premixed at a weight ratio of 1:1:0.6. This mixture is homogenized in a pulverizing mill. Thereafter, the mixture is presintered between 1 to 2 hours at 850° C. The presintered mixture is again ground in a pulverizing mill, to result in a powder, having particle sizes of, preferably, between about 1 to 10 $\mu$m. About 15% of a glass paste is added to the powder to form a binder. (The mixture of glass paste and powder will normally contain 10–20% of the glass paste). A glass paste of the Type 4011C, made by Electronic Science Laboratory (ESL), has been found particularly suitable. The resulting paste is then thinned with a thinner, added in such quantity that it can be suitable for printing, for example by application by well known thick-film technology. Suitable thinners are benzylalcohol and terpineol. The now printable paste is printed on a substrate or carrier plate made of aluminum oxide. A suitable dimension is about 6×50 mm. Double-comb-like interdigited electrodes made of gold, platinum or a palladium/silver alloy are applied on a surface of the carrier substrate and connected to suitable terminal buses. The paste is applied over the substrate by printing. Preferably, each of the electrodes is formed with about 50 teeth.

After 15 minutes of intermediate drying at 100° C., the sensor layer is fired on the substrate by exposure to a temperature of about 550° C. for one hour. (The firing step will normally be carried out in the range of 550° C. to 850° C.).

Figure 2:
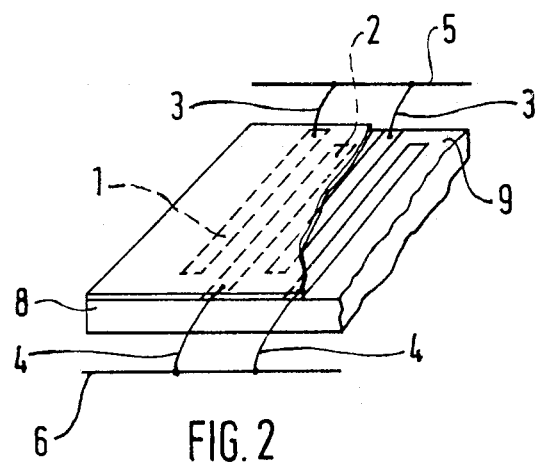
FIG. 2 is a fragmentary perspective and partly schematic view of the sensor structure.

FIG. 2 illustrates, schematically, the capacitative sensor structure. A substrate 8 has electrodes 1, 2 applied thereon, for example by printing or other technologies; the electrodes 1, 2 are connected by bonding wires 3, 4 to terminal buses 5, 6. The fired paste is shown broken away, schematically, at 9.

Figure 1:
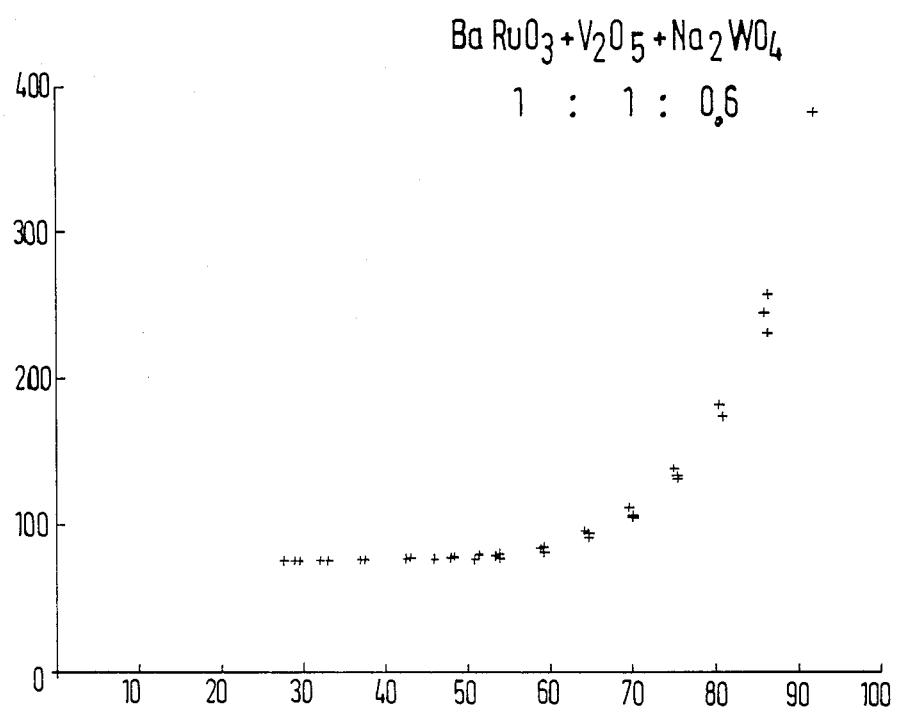
FIG. 1 is a graph illustrating the relationship of capacity (ordinate) to relative humidity (abscissa) in which the sensor has the preferred composition.
Figure 3:
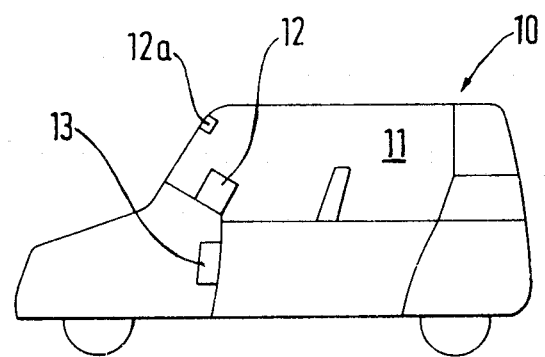
FIG. 3 illustrates an application of the sensor for use in an automotive vehicle.

The output buses 5, 6 are connected in a capacitance measuring bridge in accordance with well known capacitance measuring technology. FIG. 1 shows relationship of capacity to relative humidity. The curves were stable over about 1000 changes of humidity between 30 and 95% relative humidity. A suitable range of relative humidity for which the sensor is particularly applicable is between 60 and 95% relative humidity.

A sensor of this type is particularly suitable for use in automotive vehicles. For example, the sensor of FIG. 2 can be placed as a sensor element 12 in the passenger compartment 11 of a vehicle 10, or a similar sensor 12a can be applied to the inside of the windshield of a vehicle. Use as a fogging detector is particularly desirable, since the sensor can be readily coupled to an evaluation circuit shown schematically only at 13, for example a bridge circuit which, when a certain unbalance is reached, provides an output signal to automatically engage a defroster switch to blow defrosting air against the windshield, and thus prevent fogging before the operator's vision is impaired.

The graphic relationships of FIG. 1 clearly show that the variation in output signal is most easily detected in the range of between 60 to 90% or 95% relative humidity. By using high-precision output sensing circuits, the range of relative humidity which can be detected by the sensor can be extended. The particular advantage of non-saturation of the sensor, or, in other words, of responding to changes in humidity without exhibiting saturation or remanent phenomena is particularly important in many applications.

We claim:

1. A method of making a capacitative-type humidity sensor, to measure relative humidity by change of capacitance between two electrodes located on a substrate, in which a ceramic material is applied between the electrodes, comprising the steps of homogenizing a mixture of $BaRuO_3$, $V_2O_5$ and $Na_2WO_4$;

presintering said homogenized mixture;

adding the presintered mixture to a glass paste to form an application paste;

applying the application paste between said two electrodes; and firing the substrate with the electrodes and the application paste to form said ceramic material.

2. The method of claim 1, wherein said step of applying the application paste comprises applying said application paste by thick-film technology.

3. The method of claim 1, wherein the mixture is present in a ratio of about 1:1:0.6 by weight;

said presintering step is carried out at about 850° C.;

the presintered mixture is ground to a powder;

the step of adding the presintered mixture to the glass paste comprises adding said powder to said glass paste to provide a mixture having 10 to 20% of glass paste;

and wherein said firing step is carried out between about 550° C. to 850° C.

4. The method of claim 3, further comprising the step of adding a thinner to the glass paste until the resulting glass paste, powder and thinner is capable of being printed by thick-film technology.

5. The method of claim 5, wherein the substrate (8) comprises $Al_2O_3$, and the electrodes are applied to a surface thereof in interdigited or double-comb form.

6. The method of claim 1, wherein $BaRuO_3$, $V_2O_5$ and $Na_2WO_4$ are present in a relationship, by weight, of $(1\pm0.4):(1\pm0.4):(0.6\pm0.2)$.

7. A mixture for manufacturing a capacitative-type humidity sensor, wherein the mixture is applied between two capacitative measuring electrodes and fired, said mixture comprising a mixture of ceramic material consisting essentially of $BaRuO_3$, $V_2O_5$ and $Na_2WO_4$ with glass paste.

8. The mixture of claim 7, wherein the components of the mixture are present in a proportion—by weight—of $(1\pm0.4):(1\pm0.4):(0.6\pm0.2)$.

9. The mixture of claim 7, wherein the components of the mixture are present in a proportion—by weight—of 1:1:0.6.

10. A capacitative-type relative humidity sensor comprising a ceramic substrate;

two interdigited double-comb electrodes applied to the substrate;

and a homogenized thick-film ceramic located between said electrodes comprising a fired mixture of $BaRuO_3$, $V_2O_5$ and $Na_2WO_4$.

11. The sensor of claim 10, wherein the components of the mixture are present in a proportion—by weight—of $(1\pm0.4):(1\pm0.4):(0.6\pm0.2)$.

12. The sensor of claim 10, wherein the components of the mixture are present in a proportion—by weight—of 1:1:0.6.

13. In an automotive vehicle, a capacitative-type humidity sensor positioned within the passenger copartment of the vehicle, said humidity sensor comprising a ceramic substrate plate;

interdigited comb-like electrodes applied to the surface of said plate;

and a ceramic material on said substrate plate between said electrodes, said ceramic material comprising a fired powder mixture of $BaRuO_3$, $V_2O_5$ and $Na_2WO_4$, and a glass paste to form said ceramic material, which changes the capacitance between the electrodes upon change in ambient humidity in said passenger compartment.

14. The sensor of claim 13, wherein said sensor is applied to the windshield of the motor vehicle to form a fogging sensor for the windshield.

15. The sensor of claim 13, wherein the components of the mixture are present in a proportion—by weight—of $(1\pm0.4):(1\pm0.4):(0.6\pm0.2)$.

16. The sensor of claim 13, wherein the components of the mixture are present in a proportion—by weight—of 1:1:0.6.

* * * * *